(12) United States Patent
Hultgren et al.

(10) Patent No.: US 6,495,539 B1
(45) Date of Patent: Dec. 17, 2002

(54) B-LACTAM-LIKE CHAPERONE INHIBITORS

(75) Inventors: Scott J. Hultgren, Ballwin, MO (US); Fredrik Almqvist, Umea (SE); Gabriel Soto, Chesterfield, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 09/252,792

(22) Filed: Feb. 19, 1999

Related U.S. Application Data

(60) Provisional application No. 60/075,264, filed on Feb. 19, 1998.

(51) Int. Cl.[7] .................. C07D 501/00; C07D 499/881; C07D 499/87; A61K 31/43; A61P 31/04
(52) U.S. Cl. ...................... 514/192; 514/194; 514/195; 514/197; 540/205; 540/301; 540/302; 540/310; 540/347; 540/215; 548/201; 436/547; 435/DIG. 34; 435/DIG. 49
(58) Field of Search ................................ 514/192, 195, 514/194, 197; 540/310

(56) References Cited

U.S. PATENT DOCUMENTS

| | | | |
|---|---|---|---|
| 4,600,781 A | 7/1986 | Wolff | 548/201 |
| 5,624,677 A | 4/1997 | El-Rashidy et al. | 424/435 |
| 5,736,412 A | 4/1998 | Zambias et al. | 436/518 |
| 5,840,500 A | 11/1998 | Pei et al. | 436/501 |
| 5,847,150 A | 12/1998 | Dorwald | 548/146 |
| 5,852,028 A | 12/1998 | Suto et al. | 514/275 |
| 5,856,107 A | 1/1999 | Ostresh et al. | 435/7.1 |
| 5,856,496 A | 1/1999 | Fagnola et al. | 546/272.4 |
| 5,859,027 A | 1/1999 | Kruse et al. | 514/315 |
| 5,861,532 A | 1/1999 | Brown et al. | 564/142 |

FOREIGN PATENT DOCUMENTS

| | | |
|---|---|---|
| EP | 0 033 151 | 8/1981 |
| EP | 0 213 785 | 3/1987 |
| FR | 3 184 M | 4/1965 |
| FR | 2 547 728 | 12/1984 |
| WO | 94/03168 | * 2/1994 |
| WO | WO 94/24303 | 10/1994 |

OTHER PUBLICATIONS

Pfaendler, in "Recent Advances in the Chemistry of Beta-Lactam Antibiotics" pp. 368–378, Jun. 1980.*
Almqvist et al., "Efficient Regioselective Synthesis of Enantiomerically Pure 4–Hydroxymenthyl . . .", Tetrahedron Letters 39 (1998) 2293–2294.
Gabriel E. Soto et al., "Periplasmic Chaperone Recognition Motif of Subunits Mediates Quaternary Interactions in the Pilus", The EMBO Journal, vol. 17, No. 21, pp. 6155–6167, 1998.
Gilchrist et al., "Collaborative Study Comparing the Spiral Plate and Aerobic Plate Count Methods", J. Assoc. Anal Chem. (1977) 60:807.
Karlsson et al., "Binding of Peptides in Solution by the *Escherichia coli* Chaperone PapD as Revealed Using an Inhibition ELISA and NMR Spectroscopy", Bioorganic & Medicinal Chemistry 6 (1998) 2085–2101.
Kuehn et al., "Structural Basis of Pilus Subunit Recognition by the PapD Chaperone", Science, vol. 262, Nov. 19, 1993.
Mata, "B–Lactams on Solid Support: Mild and Efficient Removal of Penicillin Derivatives from Merrifield Resin using Aluminum Chloride" (1997) vol. 38, No. 36, pp. 6335–6338.

(List continued on next page.)

Primary Examiner—Mark L Berch
(74) Attorney, Agent, or Firm—Morrison & Foerster LLP

(57) ABSTRACT

Compounds of the formula

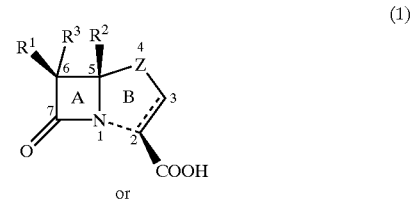

or

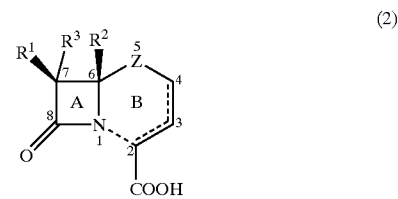

and the salts, esters and amides thereof
wherein

Z is S, SO, $SO_2$ or O;

each of $R^1$, $R^2$ and $R^3$ is independently H or substituted or unsubstituted alkyl (1–10C), substituted or unsubstituted alkenyl, substituted or unsubstituted acyl (2–11C), substituted or unsubstituted aryl (6–14C), substituted or unsubstituted arylcarbonyl (7–15C), substituted or unsubstituted arylalkyl (7–15C), substituted or unsubstituted pyridyl wherein substituents on any alkyl, alkenyl, or acyl moiety are selected from the group consisting of halo, and RO, wherein R is H or alkyl (1–6C), and substituents on any aryl or pyridyl moiety are selected from the group consisting of halo, and RO, where R is H or alkyl (1–6C), —CN and —$CF_3$; with the proviso that $R^1$ is not H and $R^1$ and $R^3$ are not identical and with the proviso that in formula (1), the B ring may contain one double bond that is located between positions 2 and 3, and in formula (2), the B ring may contain one double bond that can be located between positions 2 and 3 or positions 3 and 4 are useful as antibacterial agents.

16 Claims, No Drawings

OTHER PUBLICATIONS

Hamilakis "Acylaminoacetyl Derivatives of Active Methylene Compounds...", J. Heterocyclic Chem., 33, 825 (1996).

Striker et al., "Structural Requirements for the Glycolipid Receptor of Human Uropathogenic *Escherichia coli*", Molecular Microbiology (1995), 16(5), 1021–1029.

Yamamoto et al., "1,3–Oxazines and Related Compounds . . .", Chem. Pharm. Bull. 35(5)1871–1879, 1987.

Yamamoto et al., "1,3–Oxazines and Related Compounds XIII . . .", Chem. Pharm. Bull. 35(5) 1860–1870 (1987).

Asinger et al., *"Die Gemeinsame Einwirkung von Schwefel und Ammoniak auf Ketocarbonsauren BZW Deren Ester"*, Justus Liebigs Annalen Der Chemie, 615:84–88 (1958).

Barrett et al., "*Cationic Iron Vinylidene Complexes in Bicyclic β–Lactam Synthesis*", J. Org. Chem., 52:3940–3941 (1987).

Lorimez, Chemical Abstracts, vol. 119, No. 9, Abstract #88991 (1993).

Gioffin, Chemical Abstracts, vol. 125, No. 21, Abstract #268435 (1996).

Tera, Chemical Abstracts, vol. 80, No. 21, Abstract #120970 (1974).

Chiba et al., "*Studies on Amino Acid Derivatives, IX. Synthesis of Chiral Penam–3–carboxylic Acid and Its Substituted Derivatives*", Chem. Pharm. Bull. 37(4):877–882 (1989).

Durkin et al., "a New Model Parameter Set for β–Lactams", J. Org. Chem. 54:5839–41 (1989).

Int'l Search Report for International Application No. PCT/US99/03578 dated Oct. 28, 1999.

* cited by examiner

B-LACTAM-LIKE CHAPERONE INHIBITORS

CROSS REFERENCE TO RELATED APPLICATIONS

This application claims priority under 35 U.S.C. §119(e) to U.S. Ser. No. 60/075,264 filed Feb. 19, 1998, the contents of which are incorporated herein by reference.

STATEMENT OF RIGHTS TO INVENTIONS MADE UNDER FEDERALLY SPONSORED RESEARCH

The invention herein was made in part with support from the U.S. government. The U.S. Government has certain rights in this invention.

TECHNICAL FIELD

The invention relates to antibiotics. Novel β-lactams of the invention and compositions containing them inhibit or prevent bacterial growth and/or attachment to host tissue.

BACKGROUND ART

β-Lactam antibiotics, such as the penicillins, are known in the art. As use of these and other antibiotics has become more prevalent, resistant strains of bacteria have emerged and the need to develop new antibiotics has become apparent. The present invention is directed to a novel class of β-lactam compounds which are effective against bacterial infection, colonization and/or growth in any environment in which such prevention or inhibition is desirable.

Periplasmic chaperones are required for assembly of virulence associated pili in pathogenic, gram-negative bacteria. Pili occur on the surface of these bacteria and allow the bacteria to colonize host tissue and give rise to infections. The pili are protein fibers that present adhesions that attach to receptors that are found in the host.

The development of compounds that interfere with bacterial protein secretions constitutes an attractive approach to overcome wide-spread bacterial resistance to existing antibiotics.

The contents of all publications and U.S. patents and patent applications referred to hereinafter are hereby incorporated by reference to the extent necessary to understand or complete the disclosure of the present invention and to the same extent as though each were individually so incorporated.

DISCLOSURE OF THE INVENTION

The invention is directed generally to compounds of the formula

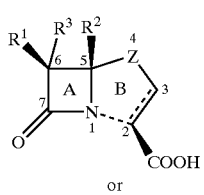

or

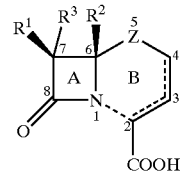

and the salts, esters and amides thereof wherein Z is S, SO, $SO_2$ or O;

each of $R^1$, $R^2$ and $R^3$ is independently h or substituted or unsubstituted alkyl (1–10C), substituted or unsubstituted acyl (2–11C), substituted or unsubstituted aryl (6–14C), substituted or unsubstituted arylcarbonyl (7–15C), substituted or unsubstituted arylalkyl (7–15C) wherein substituents on any alkyl or acyl moiety are selected from the group consisting of halo and RO, wherein R is H or alkyl (1–6C), and any substituents on any aryl moiety are selected from the group consisting of halo, —CN, $CF_3$ and RO, where R is H or alkyl with the proviso that $R^1$ cannot be H and $R^1$ and $R^3$ are not identical wherein in formula (1), the B ring may contain one double bond that is located between positions 2 and 3, in formula (2), the B ring may contain one double bond that can be located between positions 2 and 3 or positions 3 and 4.

The A and B rings have been numbered for the purpose of this application. This numbering may vary from that of IUPAC. The named compounds employ numbering consistent with IUPAC which may vary from the internal numbering scheme for the A and B rings.

In additional aspects, the invention is directed to methods to inhibit or prevent bacterial growth using the compounds of the invention, to antibodies specific for them and to antimicrobial compositions, including pharmaceutical compositions containing these compounds.

Further, the compounds of the invention are useful as scaffolds for the generation of libraries using combinatorial techniques. The libraries would be screened for desirable prospects using assays, those for antichaperone activity or antimicrobial activity.

MODES OF CARRYING OUT THE INVENTION

The present invention provides novel class of β-lactams which are effective in treating or preventing bacterial infections. Without intending to be bound by any theory, applicants believe that the compounds of the invention exert their effects by interfering with the function of chaperones required for the assembly of pili from pilus subunits in diverse Gram-negative bacteria. Such interference is particularly effective since the formation of pili is essential to bacterial pathogenicity and since the production of pilus subunits in the absence of chaperones is known to be directly toxic.

The novel compounds of the invention comprise (1S,2R,5S)-7-oxo-4-thia-1-azabicyclo[3.2.0]heptane-2-carboxylic acid and its derivatives, the corresponding compounds where S is replaced by O or by SO or $SO_2$, and their six-membered ring analogs.

The active forms of the compounds of the invention are those wherein the chirality of the nitrogen at position 1 is "S", the chirality of the carbon at position 2 is "R", the chirality of the carbon at position 5 is "S", and the chirality of the carbon at position 6 is "R" in the specific parent compound described above. The same stereochemistry is retained in the analogous compounds and derivatives although the designation of the chirality at each position may be different depending on the specific substitutions made. Accordingly, the appropriate stereoisomer can be determined by referring to formula (1). As long as this stereochemical form is present, the formulation will be active. The invention, of course, includes racemic mixtures which include this stereoisomer as well as mixtures of the various diastereomers, as long as this particular form is included.

Included in such derivatives are the salts, especially pharmaceutically acceptable salts.

Salts of carboxylic acids include those derived from inorganic bases such as the sodium, potassium, lithium, ammonium, calcium, magnesium, zinc, aluminum, and iron salts and the like, as well as those derived from organic, especially nontoxic, bases such as the primary, secondary and tertiary amines, substituted amines including naturally occurring substituted amines, cyclic amines and basic ion-exchange resins. Examples of such compounds capable of forming salts are isopropyl amine, trimethyl amine, triethyl amine, 2-dimethyl aminoethanol, dicyclohexyl amine, amino acids such as lysine, arginine and histidine, caffeine, procaine, betaene, theobromine, purines, piperazines, and the like.

As the compounds of the invention may themselves contain amino groups, the acid addition salts are also included in the scope of the invention. Such acid addition salts can be formed from inorganic acids such as hydrochloric, sulfuric, and phosphoric acid or from organic acids such as acetic, propionic, glutamic, glutaric, as well as acid ion-exchange resins.

The compounds of formula (1) including (1a) and (1b) may also be in esterified form. Typically, the esters are prepared from a hydrocarbyl alcohol. By "hydrocarbyl" is meant a monovalent substituent containing only carbon and hydrogen which may be straight or branched chain, saturated or unsaturated, aromatic or nonaromatic or both and can be cyclic or noncyclic. Thus, hydrocarbyl alcohol of 1–10C could include cyclopentyl ethyl alcohol, 2-pentanyl alcohol, 3-butynyl alcohol, 2,4-dimethyl hexyl alcohol, benzyl alcohol and the like. Particularly preferred are alkyl alcohols. "Alkyl" refers to a saturated straight or branched chain hydrocarbon which may, if it contains a sufficient number of carbon atoms, be cyclic or contain a cyclic portion. Typical examples include methyl, ethyl, t-butyl, cyclohexyl and the like. The alkyl esters of the compounds of formula are particularly preferred, especially alkyl esters wherein the alcohol contains 1–4C.

Suitable embodiments of $R^1$, $R^2$ and $R^3$ include substituted or unsubstituted alkyl (1–10C), substituted or unsubstituted acyl (2–11C), substituted or unsubstituted aryl (6–14C), substituted or unsubstituted pyridyl, substituted or unsubstituted arylcarbonyl (7–15C), substituted or unsubstituted arylalkyl (7–15C) wherein substituents on any alkyl moiety are selected from the group consisting of halo, and RO, wherein R is H or alkyl (1–6C) and substituents on any aryl moiety are selected from the group consisting of halo, RO, where R is H or alkyl, and —CN and $CF_3$. Particularly preferred are embodiments wherein $R^1$ is unsubstituted phenyl carbonyl or substituted phenyl carbonyl wherein said substituents are selected from the group consisting of lower alkyl (1–4C) and halo.

Embodiments wherein $R^2$ is alkyl (1–6C) or H are also preferred.

Also preferred are embodiments having formula (1a) wherein Z is S.

Also preferred are embodiments having formula (1a) wherein Z is S or $SO_2$; $R^1$ is naphthylmethyl carbonyl or phenyl carbonyl, $R^2$ is hydrogen, benzyl, phenyl, hydroxyphenyl or pyridyl and $R^3$ is hydrogen or phenyl.

Thus, preferred among the compounds of the invention are those wherein W is selected from the group consisting of:

phenyl-CO,
4-chlorophenyl-CO,
2,4-dinitrophenyl-CO,
3-ethoxyphenyl-CO,
phenyl, and
4-ethoxyphenyl.

In the foregoing, preferred embodiments include the alkyl esters, the embodiments wherein $R^2$ is methyl or hydrogen, and Z is S.

Compositions Containing the β-Lactams and Methods of Use

The compounds of the invention are effective in inactivating a wide range of gram-negative bacteria. Accordingly, they can be used in compositions and as for materials such as foodstuffs, cosmetics, medicaments, or other materials containing nutrients for organisms. For use in such contexts, the compounds of the invention are supplied either as a single compound, in admixture with several other compounds of the invention or in admixture with additional agents. In general, as these active ingredients are preservatives in this context, they are usually present in relatively low amounts, of less than 5%, by weight of the total composition, more preferably less than 1%, still more preferably less than 0.1%.

The compounds of the invention are also useful as standards in and in used to practice these assays.

For use as antimicrobials for treatment of animal subjects, the compounds of the invention can be formulated as pharmaceutical or veterinary compositions. Depending on the subject to be treated, the mode of administration, and the type of treatment desired, e.g., prevention, prophylaxis, therapy; the compounds are formulated in ways consonant with these parameters. A summary of such techniques is found in Remington's Pharmaceutical Sciences, latest edition, Mack Publishing Co., Easton, Pa.

As used herein, "treatment" includes both prophylaxis and therapy. Thus, in treating an animal subject, the compounds of the invention may be administered to a subject already harboring a bacterial infection or in order to prevent such infection from occurring.

In general, for use in treatment, the compounds of the invention may be used alone or in combination with other antibiotics such as erythromycin, tetracycline, macrolides, for example azithromycin and the cephalosporins. Depending on the mode of administration, the compounds will be formulated into suitable compositions to permit facile delivery to the affected areas.

Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, preservatives and the like. The compounds can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifing agents, pH buffering agents and the like, such as, for example, sodium acetate, sorbitan monolaurate, and so forth.

Various sustained release systems for drugs have also been devised. See, for example, U.S. Pat. No. 5,624,677.

Systemic administration may also include relatively noninvasive methods such as the use of suppositories, transdermal patches, transmucosal delivery and intranasal administration. Oral administration is also suitable for compounds of the invention. Suitable forms include syrups, capsules, tablets, as is understood in the art.

For administration to animal or human subjects, the dosage of the compounds of the invention is typically 0.1–100 mg/kg. However, dosage levels are highly dependent on the nature of the infection, the condition of the patient, the judgment of the practitioner, and the frequency and mode of administration.

Antibodies

Antibodies to the compounds of the invention may also be produced using standard immunological techniques for production of polyclonal antisera and, if desired, immortalizing the antibody-producing cells of the immunized host for sources of monoclonal antibody production. Techniques for producing antibodies to any substance of interest are well known. It may be necessary to enhance the immunogenicity of the substance, particularly as here, where the material is a small molecule, by coupling the hapten to a carrier. Suitable carriers for this purpose include substances which do not themselves produce an immune response in the mammal to be administered the hapten-carrier conjugate. Common carriers used include keyhole limpet hemocyanin (KLH), diphtheria toxoid, serum albumin, and the viral coat protein of rotavirus, VP6. Coupling of the hapten to the carrier is effected by standard techniques such as contacting the carrier with the peptide in the presence of a dehydrating agent such as dicyclohexylcarbodiimide or through the use of linkers such as those available through Pierce Chemical Company, Chicago, Ill.

The compounds of the invention in immunogenic form are then injected into a suitable mammalian host and antibody titers in the serum are monitored.

Polyclonal antisera may be harvested when titers are sufficiently high. Alternatively, antibody-producing cells of the host such as spleen cells or peripheral blood lymphocytes may be harvested and immortalized. The immortalized cells are then cloned as individual colonies and screened for the production of the desired monoclonal antibodies. The genes encoding monoclonal antibodies secreted by selected hybridomas or other cells may be recovered, manipulated if desired, for example, to provide multiple epitope specificity or to encode a single-chain form and may be engineered for expression in alternative host cells, such as CHO cells.

Thus, as used herein, "antibodies" also includes any immunologically reactive fragment of the immunoglobulins such as Fab, Fab' and F(ab')2 fragments as well as modified immunoreactive forms such as Fv regions, which are produced by manipulation of the relevant genes (isolable, for example, from the appropriate hybridoma) including humanization of the antibody.

The antibodies of the invention are, of course, useful in immunoassays for determining the amount or presence of the invention compounds. Such assays are essential in quality controlled production of compositions containing the compounds of the invention. They may also be used as affinity ligands for purifying and/or isolating the invention compounds. Such assays may also be useful in identifying prospective compounds from libraries generated by combinatorial techniques wherein the compounds of the invention or derivatives thereof are employed as scaffolds.

Synthesis of the Invention Compounds

The compounds of the invention can conveniently be prepared using an approach illustrated by Reaction Scheme 1.

As shown in Reaction Scheme 1, the Meldrum's acid derivative of formula (3) is coupled with the thiazolidine of formula (2) to obtain the illustrative β-lactam of the invention compound 1A.

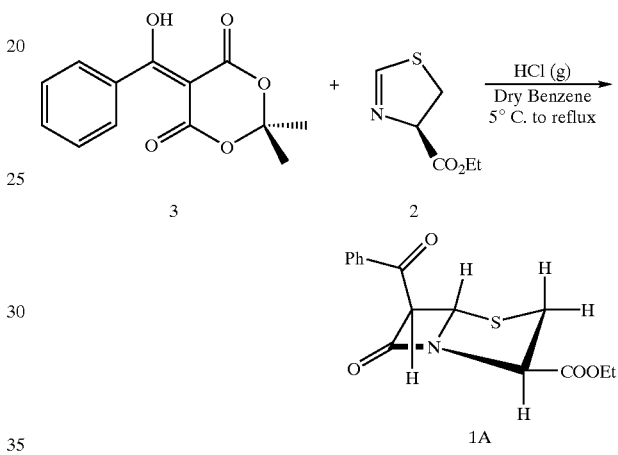

The Meldrum's acid derivative as set forth in formula (3) is obtained by condensation of a suitable carboxylic acid chloride with Meldrum's acid as illustrated in Reaction Scheme 2.

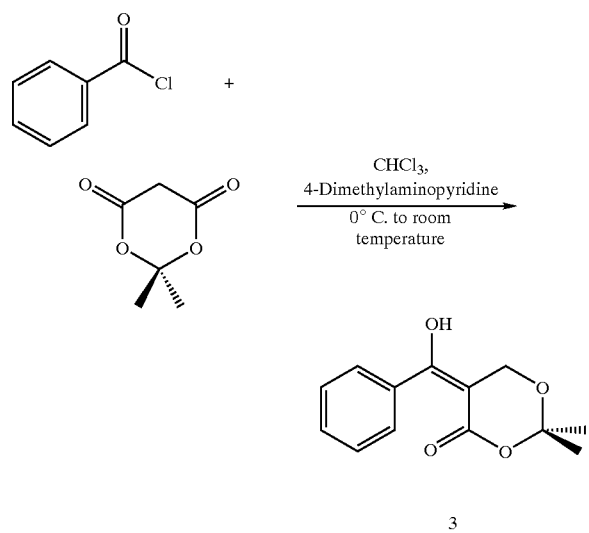

Similarly, the Meldrum's acid derivative of formula 4 is prepared as in Reaction Scheme 3, wherein the carboxylic acid, preactivated with 1,1'-carbonyldiimidazole, is condensed with Meldrum's acid.

Reaction Scheme 3

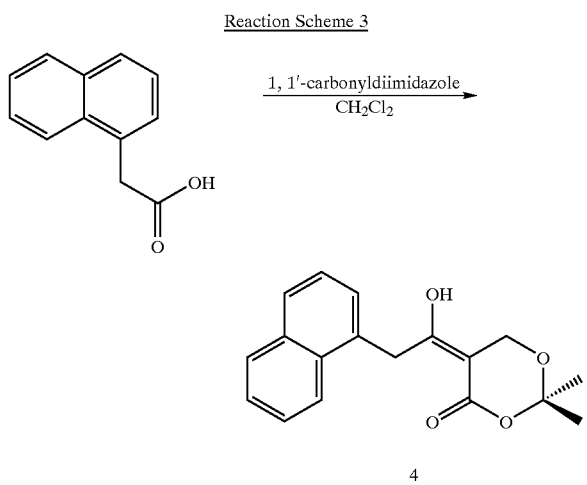

The thiazolidine derivative is prepared as shown in Reaction Scheme 4.

Reaction Scheme 4

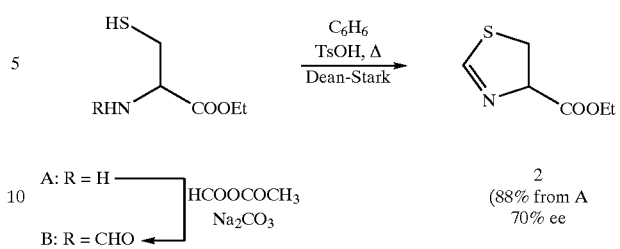

The corresponding compounds where Z is O can be prepared in an analogous manner by substituting the amino alcohol for the amino thiol.

The mono- and bi-oxidation products, Z is SO or $SO_2$, respectively, can be prepared in an analogous manner to the compounds where Z is S with the additional oxidation reactions shown in Reaction Scheme 5 ($R^1$, $R^2$ and $R^3$ are as defined above; P is a solid phase, e.g. Merrifield resin, Wang resin). See Ernesto Mata, "β-Lactams on Solid Support: Mild and Efficient Removal of Penicillin Derivatives from Merrifield Resin using Aluminum Chloride."

B-Lactams on Solid Support: Mild and Efficient Removal of Penicillin Derivatives from Merrifield Resin using Aluminum Chloride," *Tetrahedron Letters* (1997) Vol. 38, No. 36, pp. 6335–6338. The oxidation can alternatively be performed in solution. A chiral center occurs when Z is SO.

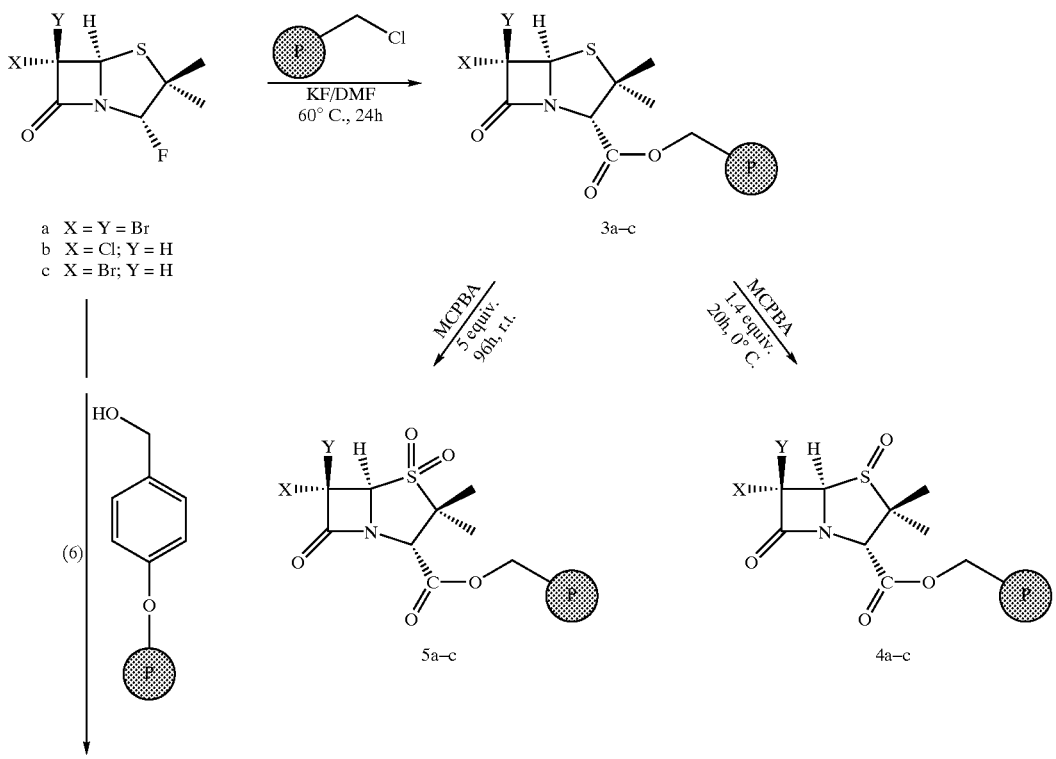

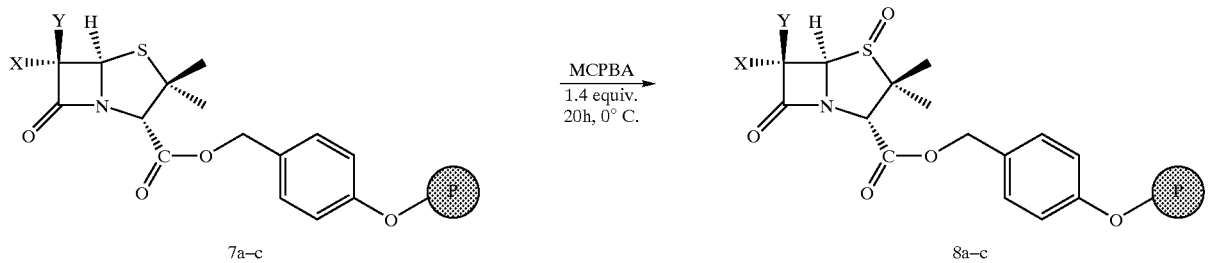

7a–c → 8a–c
MCPBA
1.4 equiv.
20h, 0° C.

In somewhat more detail, in Reaction Scheme 1, the Meldrum's acid derivative 3 is prepared as described by Yamamoto, Y. et al. *Chem Pharm Bull* (1987) 35:1871–1879, the contents of which are incorporated herein by reference. In particular, the conditions set forth on page 1876 are employed. Briefly, gaseous HCl was passed into an ice cold solution of the Meldrum's acid derivative 3 (5 mM) containing the thiazolidine derivative 2 (5 mM) in 50 ml of dry benzene until saturation. The mixture was refluxed for 1 hr and then washed with water (2×30 ml). The organic layer was dried over anhydrous Na2SO4 and concentrated under reduced pressure. The residue was then purified using silica gel column chromatography with hexane ether (1:1) as eluent to give the β-lactam product 1A. Further elution with ether provides the side-product residue of the Meldrum's acid derivative.

The Meldrum's acid derivative 3 is prepared as shown in Reaction Scheme 2 using chloroform as solvent and 4-dimethylamino pyridine as base at a temperature of 0° C. to room temperature as described in Yamamoto, Y. et al. *Chem Pharm Bull* (1987) 35:1860–1870.

Reaction Scheme 1 may also be conducted as described above but substituting for the Meldrum's acid 3, the 2-naphthylacetyl Meldrum's acid 4 prepared as set forth in Reaction Scheme 3 using methylene chloride as solvent as described in Hamilakis, S. et al. *J Heterocyclic Chem* (1996) 33:825–829, the procedure described at page 828 being incorporated herein by reference. This procedure was followed except that cold 2% KHSO4 (aqueous) was used in the workup rather than 10% HCl (aq.).

The thiazoline derivative 2 used in Reaction Scheme 1 was prepared as set forth in Reaction Scheme 4. This preparation is described by Almqvist, F. et al., *Tet Lett* (1998) 39:2293–2294. Optically pure L-ethyl cysteinate was reacted with acetyl formate to provide the formyl derivative which was then cyclized with a Dean-Stark reaction using benzene and a catalytic amount of TsOH.

Screening Assays

Antichaperone binding activity can be measured by any number of direct methods such as monitoring spectral changes in the compound and/or the chaperone, or determining the extent of compound binding to immobilized chaperone or vice versa, or by indirect methods such as competition assays to determine the extent to which these compounds inhibit chaperone binding to target pilus subunits and/or derivatives (Soto, et al., *EMBO J* (1998) 17:6155–6167) and/or synthetic peptides corresponding to subunit fragments known to bind chaperones (Kuehn, et al., *Science* (1993) 262:1234–1241; Karlsson, et al., *Bioorg Med Chem* (1998) 6:2085–2101).

Assays to determine the extent of pilus expression in the presence of these compounds would be performed as described in Soto, et al., op cit. and/or by haemagglutination assays as described in Striker, et al., *Mol Microbiol* (1995) 16:1021–1029.

Assays of inhibition of bacterial binding to target tissues in the presence of these compounds would be performed as described in Striker, et al., op cit.

Conventional techniques, e.g. radial diffusion method against *E. coli* ML-35P, *L. monocytogenes* Strain EGD and yeast phase *C. albican,* would be used to evaluate the spectra of the antimicrobial activity for the novel β-lactams of the invention.

Experimentally, the antimicrobial activity of the novel β-lactams are compared with that of the known antimicrobials against *Listeria monocytogenes* and *E. coli* by a classical colony counting technique. The antimicrobial agents were mixed with midlogarithmic phase bacteria in a sterile solution of 10 mM sodium phosphate buffer, pH 6.5 containing 0.3 mg/ml of trypticase soy broth powder. Approximately 50–100 (1 of the mixtures were incubated in a 37° C. shaking water bath and 10 (1 aliquots removed at intervals and either plated directly or diluted with a Spiral Plater (Spiral Systems Instruments, Bethesda, Md.) as described by Gilchrist, J. E. et al., *J Assoc Anal Chem* (1977) 60:807. The colonies were counted after overnight incubation.

The following examples are intended to illustrate but not to limit the invention.

EXAMPLE 1

Preparation of Thiazoline Derivatives

To a solution of 1,2-aminothiol or of L-ethyl cysteinate and Na2CO3 in a minimum volume of water, a previously prepared solution of acetic anhydride (1.05 equiv.) and formic acid (1.2 equiv.) was added. The pH of the solution was kept alkaline by addition of solid Na2CO3 and the solution was stirred for 60 min. The remaining solids were removed by filtration and the cake washed three times with CHCl3. The organic phase was neutralized (6N HCl) and concentrated. The residue was suspended in benzene, a catalytic amount of TsOH was added, and the solution was refluxed overnight using a Dean-Stark apparatus. The organic phase was evaporated, the remaining oil dissolved in CHCl3 and the organic phase washed by a saturated NaHCO3 solution. After evaporation of the organic phase, the thiazoline was purified by chromatography if necessary.

EXAMPLE 2

Preparation of Phenylcarbonyl Meldrum's Acid

A. A solution of benzoyl chloride (60 mM) in chloroform (50 ml) was added dropwise with stirring over a period of 1 hr to a solution of Meldrum's acid (7.20 g, 50 mM) and 4-dimethylamino pyridine (7.9 g, 100 mM) in chloroform (150 ml) in an ice-salt bath. The temperature was maintained for an additional 1 hr and then the reaction mixture was allowed to stand at room temperature for 1 hr. The resulting mixture was washed with 10% HCl (3×30 ml). The organic layer was separated, dried over MgSO4 and concentrated under reduced pressure. The crude product was purified by recrystallization from acetone.

The product of formula (3) was obtained in 80% yield.

B. Using the procedure set forth in Himilakis, S. et al., the compound of formula (4) was prepared in 80% yield. The procedure of Himilakis et al. was followed except that 2% KHSO4 was used in place of 10% HCl in the workup.

EXAMPLE 3

Preparation of (1S,2R,5S,6R)-6-Benzoyl-7-oxo-4-thia-1-azabicyclo[3.2.0]heptane-2-Carboxylic Acid Ethyl Ester The title compound was prepared as set forth above in the description of Reaction Scheme 1 providing the title compound as an oil in 78% yield calculated on the basis of the thiazoline 2. $[\alpha]_D+98°$. MW calculated for C15H15NO4S 305.0722. Experimental: 305.0725.

EXAMPLE 4

Preparation of (1S,2R,5S,6R)-6-Benzoyl-7-oxo-4-thia-1-azabicyclo[3.2.0]heptane-2-Carboxylic Acid Methyl Ester The title compound was prepared as set forth above in the description of Reaction Scheme 1 providing the title compound as an oil in 63% yield calculated on the basis of the thiazoline 2. $[\alpha]_D+38°$. MW calculated for C14H13NO4S:291.0565. Experimental:291.0567.

EXAMPLE 5

Preparation of Sulfoxide and Sulfone Derivatives

Using the procedure set forth in Mata, et al., the compounds of either Example 3 or Example 4 can be converted to the corresponding sulfone or sulfoxide derivative.
Synthesis of Combinatorial Libraries A number of techniques for the creation of molecular diversity exist, one of which involves the use of combinatorial techniques. Suitable combinatorial techniques include those described in U.S. Pat. Nos. 5,736,412; 5,840,500; 5,847,150; 5,852,028; 5,856,107; 5,856,496; 5,859,027 and 5,861,532. These techniques can be performed on solid or in solution phase.

The preferred process of the present invention is a "solid phase synthesis" (SPS). The reaction is carried out on macroscopic particles made of material insoluble in the reaction medium. One of the reactants, e.g., the scaffold, is linked to the surface of the support. This link is usually selected so that it positions the compound in the reaction medium. The link can be selectively cleaved in a subsequent step to release the desired product(s). Commercially available resins are suitable supports for SPS. Each derivative is usually prepared in sufficient quantity to permit screening and analysis by conventional methods, e.g., APLC and mass spectral analysis.

The array of synthesized compounds is screened using relevant assays, e.g., anti-chaperone or antimicrobial assays. The compounds are further characterized according to chemical identity and purity using conventional techniques.

The array can be scored on a real-time basis and further modifications made accordingly.

What is claimed is:

1. A compound of the formula

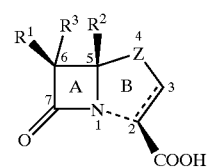

and the salts and hydrocarbyl esters of the carboxylic acid at position 2
wherein
Z is S, SO, or $SO_2$,
each of $R^1$, $R^2$ and $R^3$ is independently H, substituted or unsubstituted aryl (6–14C), substituted or unsubstituted pyridyl, substituted or unsubstituted arylcarbonyl (7–15C), substituted or unsubstituted arylalkyl (7–15C) wherein substituents on any alkyl moiety are selected from the group consisting of halo, and RO, wherein R is H or alkyl (1–6C), and substituents on any aryl or pyridyl moiety are selected from the group consisting of halo, —CN, $CF_3$, and RO, where R is H or alkyl (1–6C); with the proviso that $R^1$ is not H and $R^1$ and $R^3$ are not identical, and
wherein in formula (1), the B ring may optionally contain one double bond that is located between positions 2 and 3, as indicated by the dotted line.

2. The compound of claim 1 wherein $R^1$ is arylcarbonyl.
3. The compound of claim 2 wherein $R^1$ is unsubstituted arylcarbonyl.
4. The compound of claim 1 wherein $R^2$ is H.
5. The compound of claim 2 wherein $R^2$ is H.
6. The compound of claim 1 which is the alkyl ester of the carbonyl group at position 2.
7. The compound of claim 1 wherein Z is S.
8. The compound of claim 1 wherein $R^1$ is naphthylmethyl carbonyl or phenyl carbonyl.
9. The compound of claim 1 wherein each of $R^2$ and $R^3$ is independently hydrogen, benzyl, phenyl, hydroxyphenyl, dihydroxyphenyl or pyridinyl.
10. The compound of claim 1 wherein $R^3$ is hydrogen.
11. The compound of claim 1 contained in a mixture of its stereoisomers.
12. The compound of claim 1 in optically pure form.
13. A method to inhibit growth of Gram-negative bacteria which method comprises contacting an environment in which bacterial growth is to be prevented with the compound of claim 1 or a composition thereof.
14. A method to treat Gram-negative bacterial infection in a subject which method comprises administering to a subject in need of such treatment an effective amount of the compound of claim 1 or a pharmaceutical composition thereof.
15. A pharmaceutical composition comprising the compound of claim 1 in admixture with a pharmaceutically acceptable excipient.
16. The compound of claim 1 which is (1S,2R,5S,6R)-6-benzoyl-7-oxo-4-thia-1-azabicyclo[3.2.0]heptane-2-carboxylic acid ethyl ester.

* * * * *